(12) United States Patent
Chuck et al.

(10) Patent No.: US 7,336,989 B2
(45) Date of Patent: Feb. 26, 2008

(54) SYSTEM AND METHOD FOR QUANTITATIVE OR QUALITATIVE MEASUREMENT OF EXOGENOUS SUBSTANCES IN TISSUE AND OTHER MATERIALS USING LASER-INDUCED FLUORESCENCE SPECTROSCOPY

(75) Inventors: Roy S. Chuck, Irvine, CA (US); Peter J. McDonnell, Irvine, CA (US); Ramez Emile Necola Shehada, La Mirada, CA (US)

(73) Assignee: The Regents of the University of California, Oakland, CA (US)

( * ) Notice: Subject to any disclaimer, the term of this patent is extended or adjusted under 35 U.S.C. 154(b) by 826 days.

(21) Appl. No.: 10/407,848

(22) Filed: Apr. 3, 2003

(65) Prior Publication Data

US 2004/0199079 A1    Oct. 7, 2004

Related U.S. Application Data

(60) Provisional application No. 60/369,744, filed on Apr. 3, 2002.

(51) Int. Cl.
*A61B 6/00* (2006.01)
(52) U.S. Cl. .................. 600/477; 600/407; 600/476; 600/477
(58) Field of Classification Search ......... 600/476–477
See application file for complete search history.

(56) References Cited

U.S. PATENT DOCUMENTS

| | | | |
|---|---|---|---|
| 5,198,871 A | 3/1993 | Hill, Jr. et al. | |
| 5,337,676 A | 8/1994 | Ahad | |
| 5,419,323 A | 5/1995 | Kittrell et al. | |
| 5,562,100 A | 10/1996 | Kittrell et al. | |
| 5,634,920 A * | 6/1997 | Hohla | 606/12 |
| 5,811,446 A * | 9/1998 | Thomas | 514/399 |

OTHER PUBLICATIONS

Maldonado-Codina et al. Thermal Consequences of Photorefractive Keratectomy.Cornea 20(5): 509-515, 2001.*
David Cohen et al., "*Ablation spectra of the human cornea*", Journal of Biomedical Optics, vol. 6(3) (Jul. 2001), p. 339-343.
Roy S. Chuck et al., "*Fluorescence-guided laser removal of chemically damaged cornea*", J Cataract Refract Surg, vol. 28, (Oct. 1994), pp. 1847-1852.

* cited by examiner

*Primary Examiner*—Brian Casler
*Assistant Examiner*—Crystal I Leach
(74) *Attorney, Agent, or Firm*—Robert D. Buyan; Stout, Uxa, Buyan & Mullins LLP

(57) ABSTRACT

Methods and systems for determination of one or more substances within a material are described. A flow of fluorescence-exciting/ablative energy (e.g., laser pulse(s), preferably in the ultraviolet region (e.g. 193-nm)), is directed onto the material to ablate a thin layer of the material using photochemical decomposition. Simultaneously, the laser energy induces fluorescence of the substance(s) within the ablated layer of the material. The fluorescence emitted by the substance(s) is then received by a device, which measures the spectrum of the received fluorescence. The fluorescence spectra are then transmitted to a spectral processing device adapted to determine, on the basis of the fluorescence spectra, whether the substance(s) of interest is/are present in the material and/or the concentration at which the substance(s) of interest is/are present in the material. This process may be repeated for each layer of the material to determine the concentration gradient of the substance(s) of interest in the material.

25 Claims, 14 Drawing Sheets

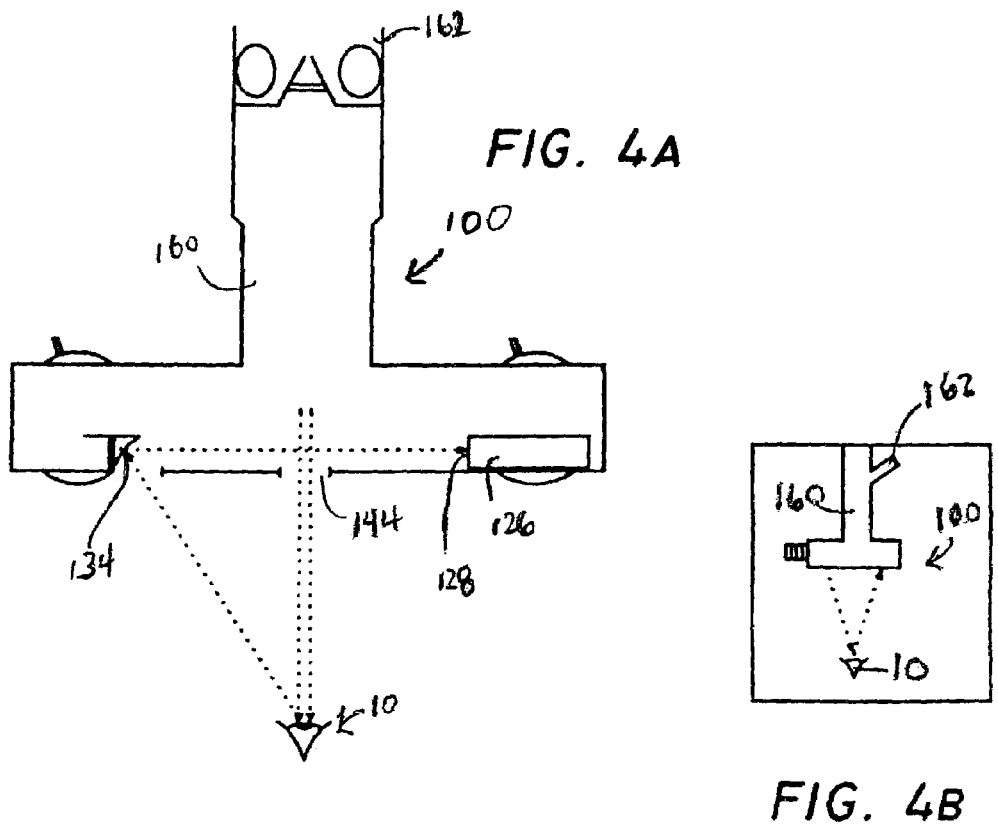
FIG. 4A
FIG. 4B
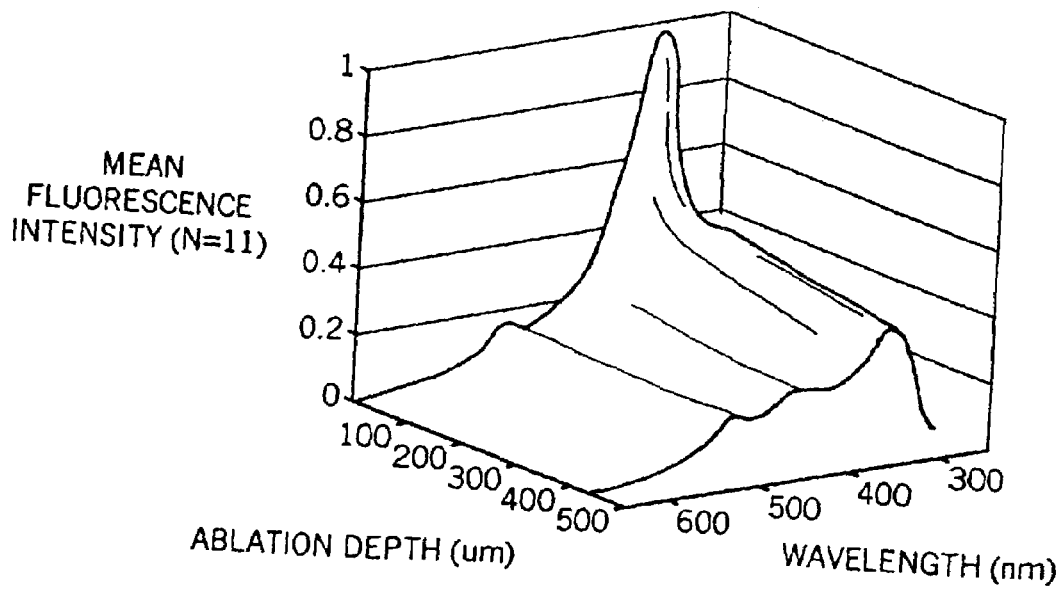
FIG. 5

SYSTEM AND METHOD FOR QUANTITATIVE OR QUALITATIVE MEASUREMENT OF EXOGENOUS SUBSTANCES IN TISSUE AND OTHER MATERIALS USING LASER-INDUCED FLUORESCENCE SPECTROSCOPY

RELATED APPLICATION

This application claims the benefit of U.S. Provisional Application Ser. No. 60/369,744 filed Apr. 3, 2002, a portion of which is expressly incorporated herein by reference.

FIELD OF THE INVENTION

The present invention generally relates to laser-induced fluorescence spectroscopy. More particularly, the invention relates to a method for determining the concentration versus the depth of absorption of an exogenous substance in a material using laser-induced fluorescence spectroscopy. In one specific embodiment, laser-induced fluorescence spectroscopy is used to determine the absorption gradient of a drug or other exogenous substance in a body tissue.

BACKGROUND OF THE INVENTION

Fluorescence is the phenomenon in which light of a given wavelength is absorbed by a fluorescent molecule (e.g., a "fluorophore"), thereby resulting in emission of light at longer wavelengths. The distribution of the wavelength-dependent intensity that causes fluorescence is known as the fluorescence excitation spectrum, and the distribution of wavelength-dependent intensity of emitted energy is known as the fluorescence emission spectrum.

Using fluorescence, one can monitor minute changes in the concentration of a substance. Changes in fluorescence intensity on the order of picoseconds can be detected if necessary. Over the past decade, investigators have proposed many new applications for fluorescence spectroscopy in the physical and life sciences in view of advances in time resolution, methods of data analysis, and improved instrumentation. With these advances, it is now practical to perform time-resolved measurements with enough resolution to compare the results with the structural and dynamic features of macromolecules, to probe the structure of proteins, membranes, and nucleic acids, and to acquire two-dimensional microscopic images of chemical or protein distributions in cell cultures. Advances in laser and detector technology have also resulted in renewed interest in fluorescence for clinical and analytical chemistry.

In a fluorescence spectrometer, the sample to be analyzed is irradiated by excitation light, which causes the sample to emit fluorescence light at characteristic wavelengths. The fluorescence light is measured by a suitable detector to derive information about the sample, in particular the composition of the sample and the quantities of the individual components present in the sample. Typically, the wavelength of the excitation light is adjusted by an optical component, such as a diffraction grating or a filter. The fluorescence light emitted is usually analyzed by a second diffraction grating or by a filter. For performing a fluorescence measurement, the grating at the excitation side of the spectrometer is set to a fixed excitation wavelength and the wavelength spectrum of the fluorescence light is recorded by means of the grating at the emission side (emission grating). The emission spectrum can be recorded for a plurality of excitation wavelengths. As an alternative thereto, the emission wavelength can be kept fixed and the excitation wavelength can be varied by corresponding adjustment of the excitation grating.

Laser induced fluorescence spectroscopy has heretofore been used to determine the chemical composition of, or pathological conditions in, biological tissue. For example, U.S. Pat. Nos. 5,419,323 (Kittrell et al.) and 5,562,100 (Kittrell et al.) describe methods for laser induced fluorescence of tissue in which laser radiation is used to illuminate and induce fluorescence in the tissue for the purpose of determining the chemical composition of, or a pathologic condition in, the tissue. The laser radiation and the retrieved fluorescing radiation can be conveyed through a catheter using an array of optical fiber. The fluorescence spectrum of the tissue can be displayed and analyzed to obtain information regarding the chemical composition and medical condition of the tissue inside the human body. Also, U.S. Pat. No. 5,337,676 (Vari et al.) describes a method for determining the biodistribution of substances using fluorescence spectroscopy wherein a photosensitizing agent or other intrinsically fluorescent agent, or an agent labeled with an extrinsic fluorophore, is administered to a subject. A fiberoptic probe integrated with an excitation light source illuminates the tissue and causes fluorescence. The fluorescence is recorded by a spectrograph and plotted as a spectral curve. The intensity ratio (S1/S2) for the fluorescence from the photosensitizing agent (S1) and autofluorescence (S2) for the examined tissue is used as an index for drug presence and compared with the intensity ratio at the same wavelengths for various tissues.

Laser induced fluorescence spectroscopy has also been used to determine the presence of certain chemicals or substances within non-biological materials. For example, U.S. Pat. No. 5,198,871 (Hill Jr., et al.) describes an optical inspection system wherein laser-induced luminescence is used to determine the quality of materials, such as fuel. The inspection system comprises an excitation means, such as a laser, for illuminating a specimen and for causing the specimen to produce fluorescent radiation. The fluorescence spectrum produced by the specimen is then compared to a reference spectrum to obtain an indication of the physical characteristics of the specimen (e.g., to determine the presence of chemical impurities or degradation products within the specimen).

SUMMARY OF THE INVENTION

The present invention provides methods and systems for quantitative and/or qualitative determination of one or more exogenous substances (e.g., specific compounds or classes of compounds that have a common chemical group, moiety, structural component or congener) within a material. A laser pulse, preferably in the ultraviolet region (e.g. 193-nm), is directed onto the material to ablate a thin layer (e.g. ≈0.3-μm) of the material using photochemical decomposition. Simultaneously, the laser pulse induces the fluorescence of the substance(s) of interest within the ablated layer of the material. The fluorescence emitted by the substance(s) of interest is then received by a device (e.g., a spectrometer), which measures the spectrum (i.e. intensity versus wavelength) of the received fluorescence. The fluorescence spectra are then transmitted to a spectral processing device (e.g., a microprocessor or computer) which is programmed or otherwise adapted to determine, on the basis of the fluorescence spectra, whether the substance(s) of interest is/are present in the material and/or the concentration at which the substance(s) of interest is/are present in the material. This process may be repeated for each layer of the material to determine the concentration gradient of the substance(s) of interest in the material.

Alternatively, the fluorescence emitted by the substance(s) of interest may be received by a device (e.g., a photomultiplier in a time-resolved fluorescence measurement system), which measures the temporal decay of the received fluorescence. The fluorescence temporal decay may be transmitted to a spectral processing device (e.g., a microprocessor or computer) which is programmed or otherwise adapted to determine, on the basis of the temporal decay characteristics, whether the substance(s) of interest is/are present in the material and/or the concentration at which the substance(s) of interest is/are present in the material.

The present invention is useable to qualitatively or quantitatively analyze for the presence of a specific chemical compound or for all compounds within the material that share a common florescence-emitting chemical group, chemical structure or congener. Examples of the types of exogenous compounds that may be detected or measured using this invention include, but are not limited to, drugs, pesticides, herbicides, contaminants, etc. The types of materials on which this technique may be performed include but are not limited to biological tissues, plant matter (e.g., fruit, produce, grain, etc.), plastics, or other industrial matrices.

In accordance with at least some embodiments of the invention, the fluorescence-exciting energy may ablate or substantially damage some portion of the material, while in other embodiments, the fluorescence-exciting energy will merely induce the desired fluorescence without ablating or causing substantial damage to the material.

Further, in accordance with at least some embodiments of the invention, the spectral processing device may be programmed to determine the presence and/or concentration of the substance of interest using spectral classification technique and/or neural networking and/or partial least squares modeling. In some embodiments where spectral classification technique is used, the received fluorescence spectra are compared to reference data (e.g., experimentally or mathematically generated reference spectra that correlate to specific substances and/or specific concentrations of substances within the material.

Still further In accordance with the invention, the method and system may be employed to determine the presence and/or amount of particular florescence-emitting drug substances (or other substances of exogenous origin) in living or dead biological tissue. In some such embodiments, a device (e.g., a laser emitting device) that emits beam or pulses of the fluorescence-exciting energy may be positioned extracorporeally in relation to the body of a patient or cadaver such that the beam or pulses of fluorescence-exciting energy is cast upon a particular tissue of the body (e.g., the cornea of the eye, skin, etc.).

Still further In accordance with the invention, the method and system may be employed to determine the presence and/or amount of particular florescence-emitting pesticides, herbicides (or other substances of exogenous origin) in living or dead plant matter. In some such embodiments, a device (e.g., a laser emitting device) that emits beam or pulses of the fluorescence-exciting energy may be positioned in relation to a quantity of plant matter (e.g., produce, fruit, growing plants, etc.) such that the beam or pulses of fluorescence-exciting energy is cast upon the plant matter causing the pesticides, herbicides or other exogenous substances of interest to fluoresce.

Further aspects and advantages of the invention will become apparent to persons of skill in the art upon reading and understanding of the detailed descriptions of the preferred embodiments set forth herebelow.

BRIEF DESCRIPTION OF THE DRAWINGS

FIG. 4A is a schematic view showing a spectral analysis system according to the present invention retrofitted into a conventional laser apparatus;

FIG. 4B is a side view of FIG. 4A;

FIG. 5 shows the mean fluorescence spectra versus ablation depth for clear normal corneas;

DETAILED DESCRIPTION AND EXAMPLES

The following detailed description, and the accompanying drawings to which it refers, are provided describing and illustrating certain examples or specific embodiments of the invention only and not for the purpose of exhaustively describing all possible embodiments and examples of the invention. Thus, this detailed description does not in any way limit the scope of the inventions claimed in this patent application or in any patent(s) issuing from this or any related application.

The following detailed description contains examples that relate to measurement of drugs or other exogenous substances in mammalian eyes. It is to be appreciated, however, that the utility of the invention is by no means limited to use on mammalian eyes. Rather, as those of skill in the art will understand, the systems and methods described in the examples herebelow may also be used with little or no adaptation or adjustment, to determine the presence or concentration of many different exogenous substances in many different types of materials, including but not limited to skin, organs, hair, nails, plant matter, vegetables, fruits, textiles, leather, water, and various other solid materials, slurries, etc. Also, some of the examples discussed herebelow describe the use of the system to determine the thickness or depth of certain tissues (e.g., layers of the cornea) of the eye on the basis of fluorescence emitting substances within those layers. These examples are provided, in part, to further enhance the reader's understanding of the use of this invention to determine the presence and/or concentration of drugs or other exogenous substances as a function of depth within a cornea or other tissue, as recited in some of the following claims.

Figure 1:
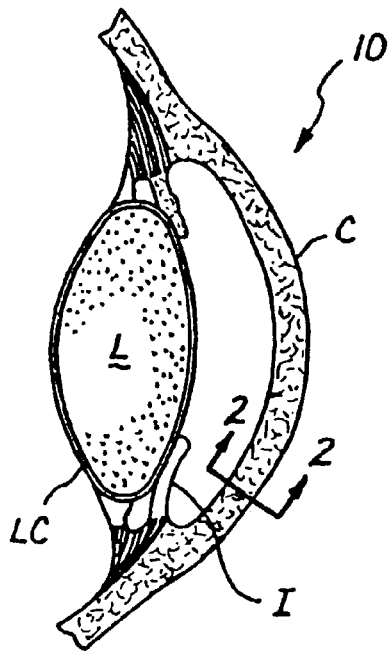
FIG. 1 is a sectional view showing the anterior portion of a human eye.

FIG. 1 of this application illustrates the anterior portion of a human eye 10. The anatomical structures of the eye 10, shown in these figures, are labeled in accordance with the following legend.

| Cornea | C |
| Anterior Chamber | AC |
| Iris | I |
| Lens Capsule | LC |
| Lens | L |

Figure 2:
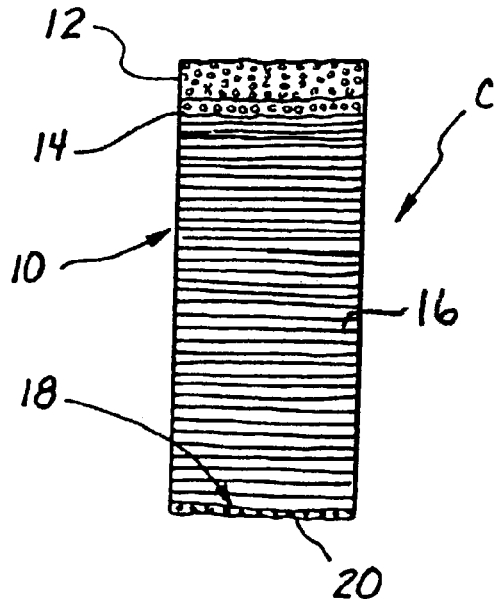
FIG. 2 is an enlarged sectional view taken through line 2-2 of FIG. 1, showing the layers of the cornea.

FIG. 2 is a sectional view through the cornea C showing its laminar structure. The anteriormost layer of the cornea C is a stratified squamous layer known as the epithelium 12. Behind the epithelium 12 is a thick basal lamina, Bowman's membrane 14. The central, and largest, layer of the cornea C is the stroma 16, which consists primarily of hundreds of layers of flattened collagenous lamellae. Behind the stroma 16 is another basal lamina, Descemet's membrane 18, and behind Descemet's membrane is a very thin, single layers of cuboidal cells called the corneal endothelium 20, which demarcates the limit of the anterior chamber AC.

A first set of experiments was performed with the objective of determining: a) whether the fluorescence of certain antibiotics interferes with the autofluorescence of ablated corneal layers; and b) a paradigm for determining the concentration of a fluorescent antibiotic in a cornea. This set of experiments is discussed in examples 1-7 below.

A second set of experiments was performed with the objective of determining a) the fluorescence spectra of various antibiotics; b) the fluorescence spectra of antibiotic treated corneas; and c) the penetration depth of antibiotics in the cornea. This set of experiments is discussed in examples 8 and 9 below.

Experimental Setup and Protocol

The first set of experiments was performed on cadaveric human corneas rejected for corneal transplantation or other clinical applications. The corneas, which were obtained from the Doheny Eye Bank, Los Angeles and the Donor Network of Arizona, can be divided into five groups as follows:

| Description | Average Age/Span (Years) | Number |
|---|---|---|
| Clear normal corneas: | | |
| The corneas are soaked for 48-h in a buffered media (Dulbecco Modified Eagle Medium) to flush Optisol ® | 67/49-85 | 11 |
| Antibiotic treated corneas: | | |
| The cornea is soaked in 0.5 µgm/ml Levofloxacin (Quixin, Santen) diluted in 3-ml Dulbecco Modified Eagle solution | 49/15-83 | 4 |
| Total number of samples | | 15 |

The second set of experiments was performed on fresh rabbit corneas. All experiments were performed in compliance with the Association for Research in Vision and Ophthalmology (ARVO) Statement on the Use of Animals in Research. Approval was obtained from the University of California, Irvine, Institutional Care and Use Committee (IACUC) and the IACUC guidelines regarding animal experimentation were followed. New Zealand White rabbit heads were obtained from an abattoir and kept at 4° C. until eyes were enucleated within 7-hours of death to maximize preservation of the corneal epithelium. The globes were stored in a moist chamber at 4° C. for approximately 4 hours until time of use.

Figure 3:
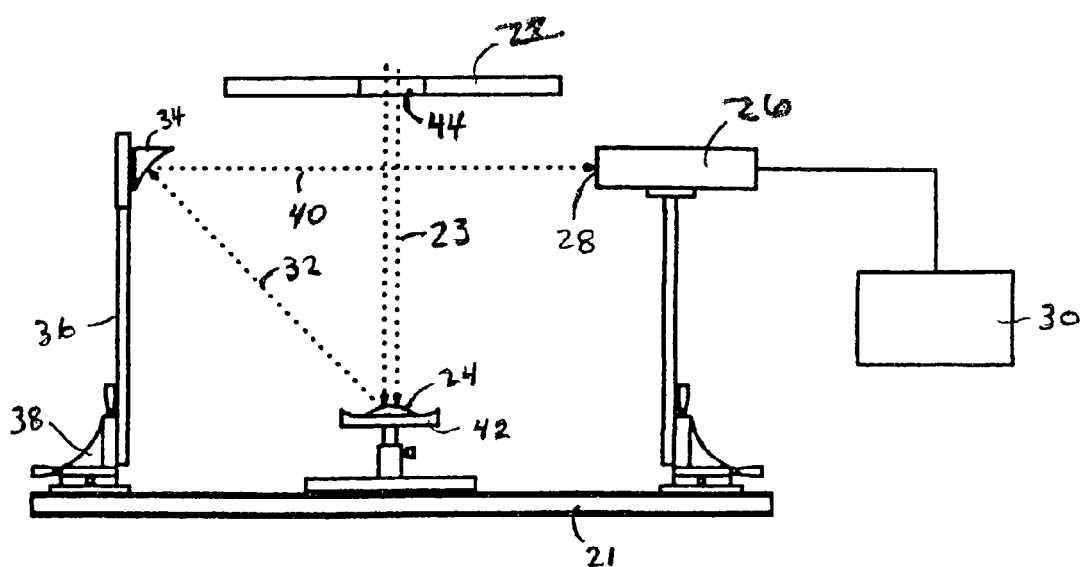
FIG. 3 is a schematic view showing an experimental spectral analysis setup according to the present invention.

A schematic diagram of the spectroscopy system used in both sets of experiments is shown in FIG. 3. The main component, mounted on or above an optical table 21, is the Nidek EC-5000 laser system 22 (Model EC-5000, Nidek Technologies, Inc., Japan) operating at 193 nm. The average laser energy is about 16.4 mJ/pulse measured over a period of 10-s while pulsing at 4 Hz. The eye-fixation LED and the aiming He—Ne laser within the laser system 22 are disabled to avoid their interference with the measured corneal autofluorescence.

During the experiments, the laser 22 is operated to emit a collimated laser beam 23 in the direction of a cornea 24. The laser 22 is operated in its manual mode to pulse the beam 23 at 4 Hz and generate a rectangular spot size of about 2×4.5-mm. The BNC cable connecting the control circuitry of the EC-5000 to the OEM XeFl excimer laser (Lambda Physik, Fort Lauderdale, Fla.) is tapped using a BNC T-adapter. This laser trigger pulse is delayed by 241.5-ms via a delay generator (Model DG535, Stanford Research Systems, Inc., Sunnyvale, Calif.) and used to trigger the spectral acquisition of a spectrograph 26 (Model SD2000, Ocean Optics, Dunedin, Fla.). This allows the appropriate timing between the delivery of the laser pulse and the spectral acquisition of spectrograph 26. The spectrograph 26 has an entrance slit 28 of 200-µm, a 600-groove/mm grating blazed at 400 nm and a 2048-pixel diode array (CCD ILX511, Sony Semiconductors, Japan) with order sorting coatings. The data acquisition system is comprised of a 1-MHz multichannel A/D board hosted in a personal computer 28 (Aptiva, AMD 800-MHz, IBM, White Plains, N.Y.).

Each pulse of radiation emitted from the laser 22 ablates a thin layer of the cornea 24. The laser-induced fluorescence (LIF) 32 produced by the ablated cornea 24 is reflected by a 2" off-axis parabolic mirror 34 (Al, SiO-protected Model A8037-331, Janos Technology Inc., Townshend, Vt.) mounted on a mirror holder 36 that is, in turn, mounted on an XYZ translator 38. The reflected LIF 40 is then focused into the entrance slit 28 of the spectrograph 26. With each trigger pulse, the spectrograph 26 measures and auto-saves the fluorescence spectrum generated by the corresponding laser pulse.

The cornea 24 was placed epithelium-up (with the exception of the cornea in Example 4) on a circular aluminum tray 42. The height of the tray 42 was adjusted to position the cornea 24 at the right distance from the laser aperture 44 using the crosshairs positioning lights of laser 22. The laser 22 was set to ablate the cornea at 4-Hz for a period of about 7-minutes and the fluorescence spectrum generated by each pulse was measured and saved. In some cases, the ablated corneas were imaged using reflection microscopy to measure the ablation rate (=total ablation depth/number of laser pulses).

Spectral Processing and Data Analysis

In each set of experiments, the measured fluorescence spectra are corrected for dark current and background light, and each spectrum is smoothed using a 5-point moving average window. The series of spectra measured from a given cornea are normalized by the peak value of the first spectrum in the series (i.e. the spectrum of the corneal surface).

The sum of absolute differences (SAD) between the first spectrum and each of the succeeding spectra is calculated. The SAD between any two spectra $I_1(\lambda)$ and $I_2(\lambda)$ is given by:

$$\sum_{\lambda=1}^{N} |I_1(\lambda) - I_2(\lambda)| \quad (1)$$

where $\lambda$ is the wavelength, N is the total number of wavelengths in the spectrum and I is the fluorescence intensity. The SAD is a measure of mismatch, where a zero SAD indicates identical spectra and vice versa.

The correlation coefficient between the first spectrum and each of the succeeding spectra is calculated. The correlation coefficient is a measure of match or resemblance, where a zero correlation coefficient indicates total spectral mismatch and vice versa.

In addition, the skewness, kurtosis, percentiles, area and mean value of each spectrum are calculated for each of the spectra. Changes in the correlation coefficient, SAD, skewness, kurtosis, percentiles, area and mean value of each spectrum are used to determine relative changes in concentration.

In addition, the partial least squares technique (PLS) is applied to develop a model for the detection of a drug concentration. The model inputs and outputs were the measured fluorescence spectra and their corresponding drug concentrations, respectively. As a preliminary step in the model development process, the fluorescence spectra of the different drug concentrations were statistically compared to identify the wavelength band where the spectral profiles are most distinct. This band ranged between 250 and 655-nm approximately and each spectrum is resampled every 5-nm to reduce the number of spectral points to 76. For each antibiotic tested, a PLS model is developed for the discrimination between normal and antibiotic treated corneas. The inputs of each model are the first 200 fluorescence spectra acquired from normal cornea and the first two fluorescence spectra acquired from corneas treated with a known concentration of the antibiotic. The first 200 spectra from normal cornea arise from both epithelial and stromal tissue within the anterior 60-μm approximately. The first two spectra from antibiotic treated corneas are chosen because their spectral profile resembled that of antibiotic and represented antibiotic-saturated cornea.

The optimal rank of the PLS model was selected as the lowest rank yielding the minimal prediction error. In a second rank selection method, the reduced eigenvalues of the data matrix were calculated according to the method of Malinowski [3]. The optimal rank should be equal to the number of significant reduced eigenvalues. The latter were arranged in descending order of significance and the two-way F-test was used to check for a 95% significant difference between successive reduced eigenvalues. The PLS rank of 8 was found to be optimal.

The PLS modeling algorithms were implemented using the scientific application environment MATLAB (Version 5.3, The MathWorks, Inc. Natick, Mass.). The optimized PLS model was evaluated for its discrimination accuracy using the method of cross-validation. In the latter, one input-output pair was excluded from the input-output data matrix used in estimating the model. The excluded input-output pair was used to validate the model by testing its ability to predict the correct output from the input that was not involved in the model estimation. The above process was repeated for each input-output pair in the data matrix and the accuracy of the model in predicting the tissue type was calculated by dividing the number of correct predictions by the total number of predictions. The cross-validated detection accuracy of the antibiotic presences was 100% in each case with detection sensitivity of better than 0.06-μg/ml.

EXAMPLES

Example 1

The mean fluorescence spectra of eleven clear normal corneas were generated using the experimental protocol and spectral processing methods described above. The spectra are plotted versus ablation depth in the three-dimensional plot shown in FIG. 5.

Example 2

Figure 6A:
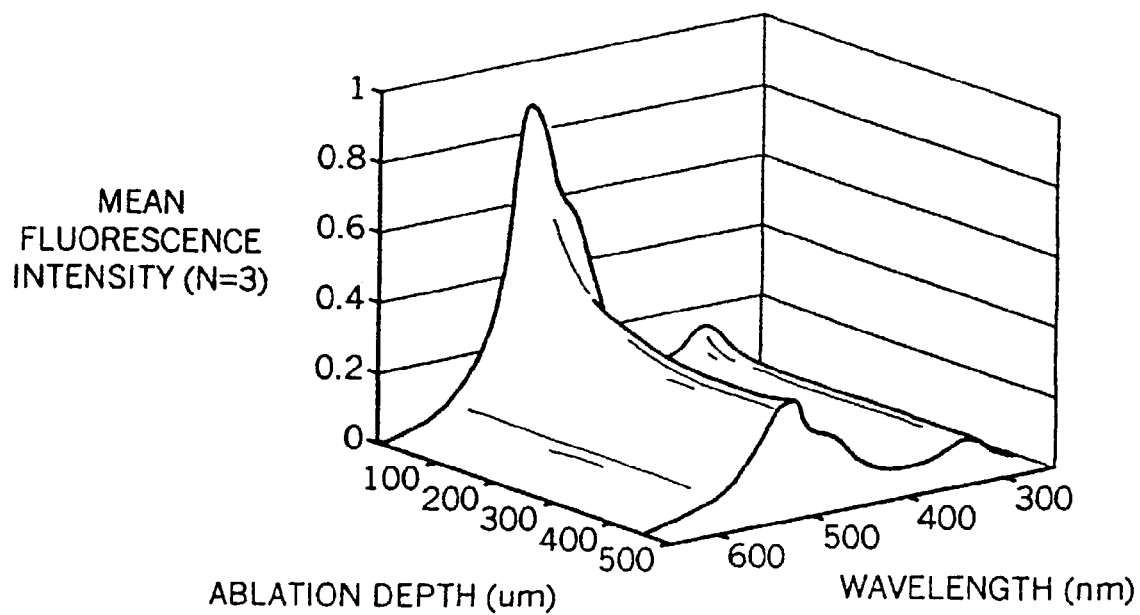
FIGS. 6A and B show the mean fluorescence spectra versus ablation depth for (a) normal corneas having a high concentration of levofloxacin; and (b) normal corneas having a low concentration of levofloxacin.

The mean fluorescence spectra of three normal corneas soaked in levofloxacin for 48 hours, representing high concentration, were generated using the experimental protocol and spectral processing methods described above. The mean spectra are plotted versus ablation depth in the three-dimensional plot shown in FIG. 6A.

Example 3

Figure 6B:
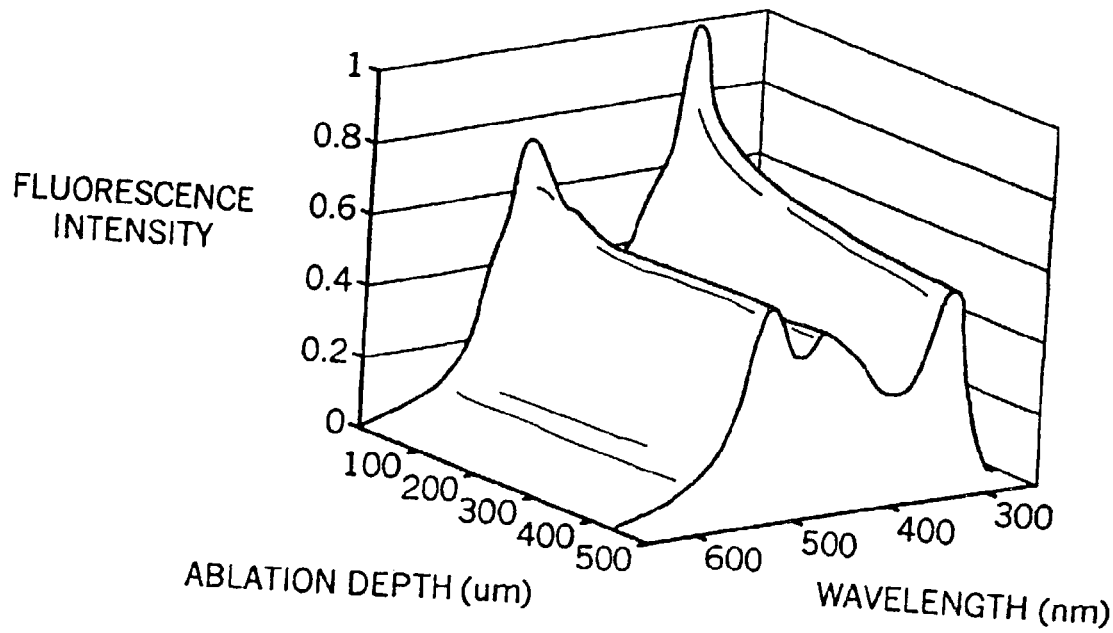

The mean fluorescence spectra of one normal cornea soaked in levofloxacin for one second and then flushed with normal saline solution, representing low concentration, were generated using the experimental protocol and spectral processing methods described above. The spectra are plotted versus ablation depth in the three-dimensional plot shown in FIG. 6B.

Example 4

Figure 7A:
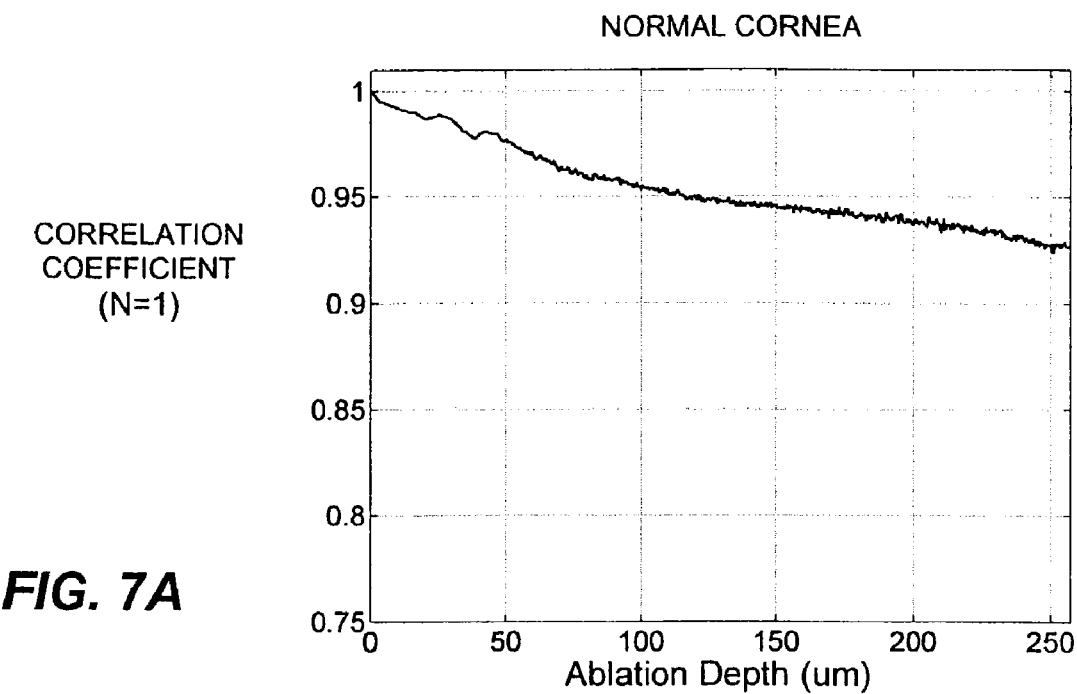
FIGS. 7A and B show the correlation coefficient versus ablation depth for (a) clear normal corneas; and (b) cornea with levofloxacin.

The correlation coefficient between the first spectrum and each of the succeeding spectra are calculated and plotted versus the ablation depth for a clear normal cornea. The results are shown in FIG. 7A.

Figure 7B:
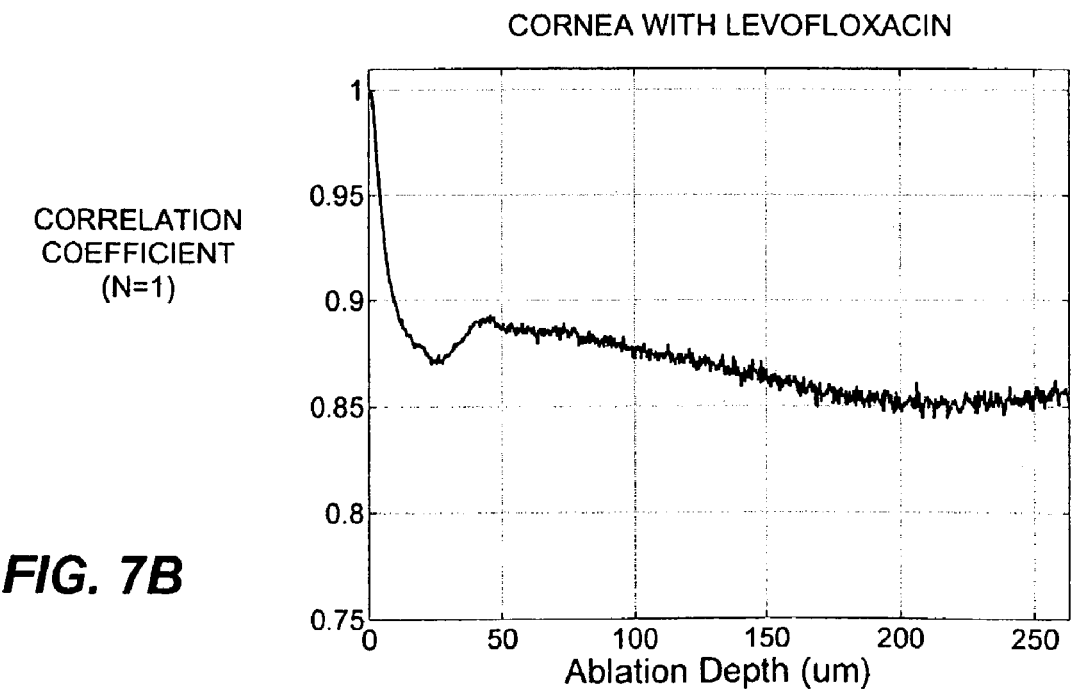

The correlation coefficient between the first spectrum and each of the succeeding spectra are calculated and plotted versus the ablation depth for levofloxacin treated cornea. The results are shown in FIG. 7B.

Example 5

Figure 8A:
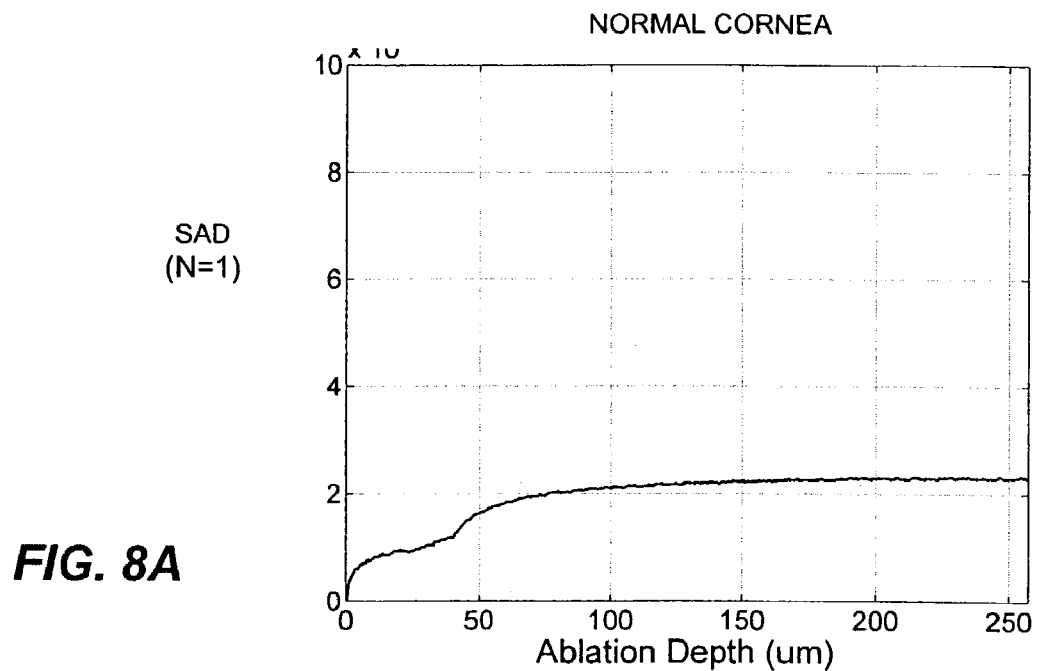
FIGS. 8A and B show the sum of absolute differences (SAD) versus ablation depth for (a) clear normal corneas; and (b) cornea with levofloxacin.

The SAD between the first spectrum and each of the succeeding spectra are calculated and plotted versus the ablation depth for a clear normal cornea. The results are shown in FIG. 8A.

Figure 8B:
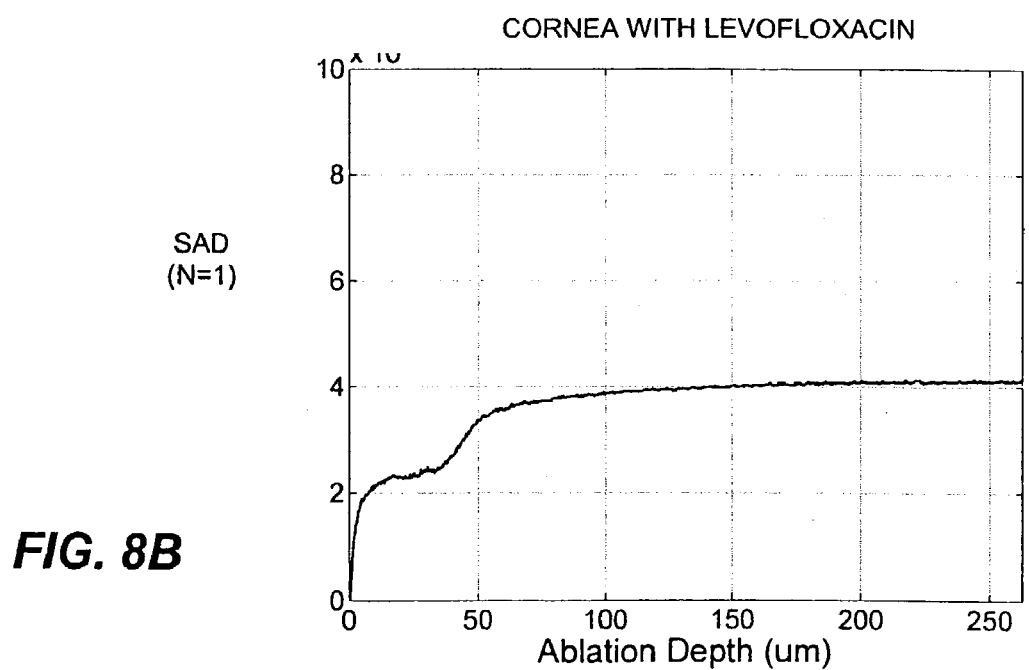

The SAD between the first spectrum and each of the succeeding spectra are calculated and plotted versus the ablation depth for levofloxacin treated cornea. The results are shown in FIG. 8B.

Example 6

Figure 9A:
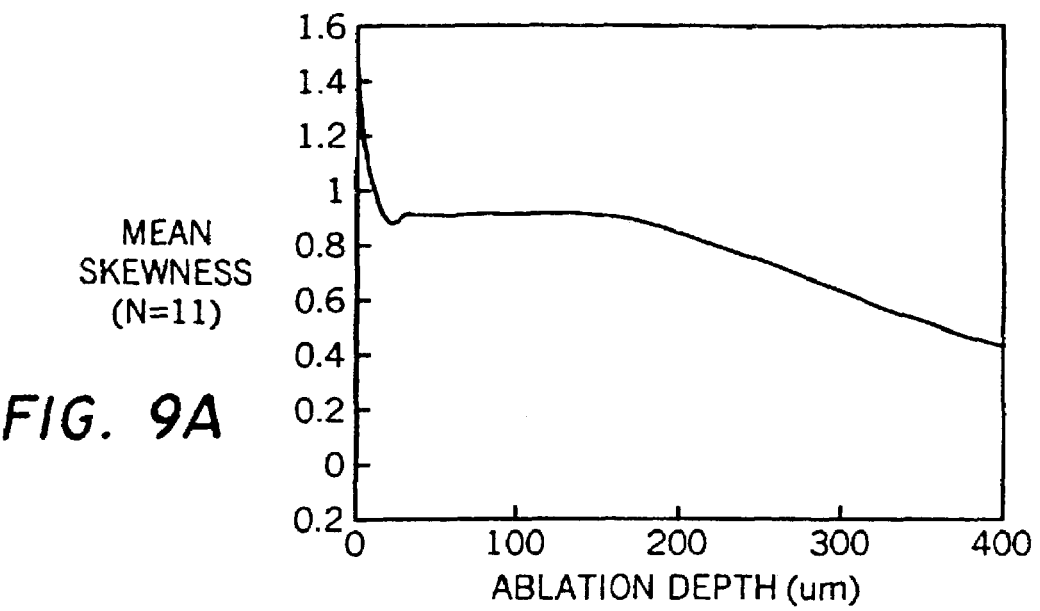
FIGS. 9A and B show the mean (a) skewness and (b) kurtosis versus ablation depth for clear normal corneas.

The mean skewness was calculated and plotted versus the ablation depth for the eleven clear normal corneas used in Example 1. The results are shown in FIG. 9A.

Figure 9B:
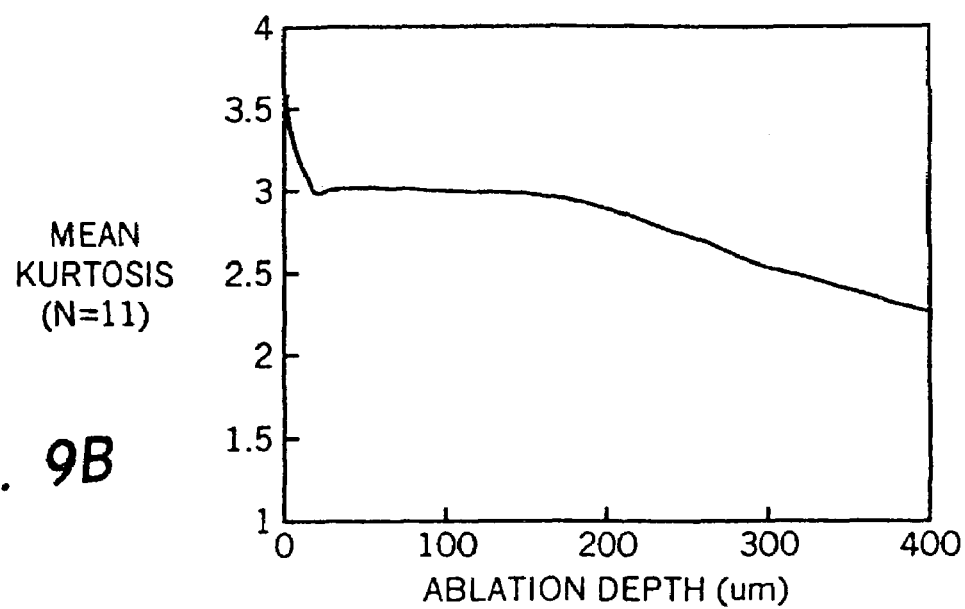

The mean kurtosis was calculated and plotted versus the ablation depth for the eleven clear normal corneas used in Example 1. The results are shown in FIG. 9B.

Example 7

Figure 10:
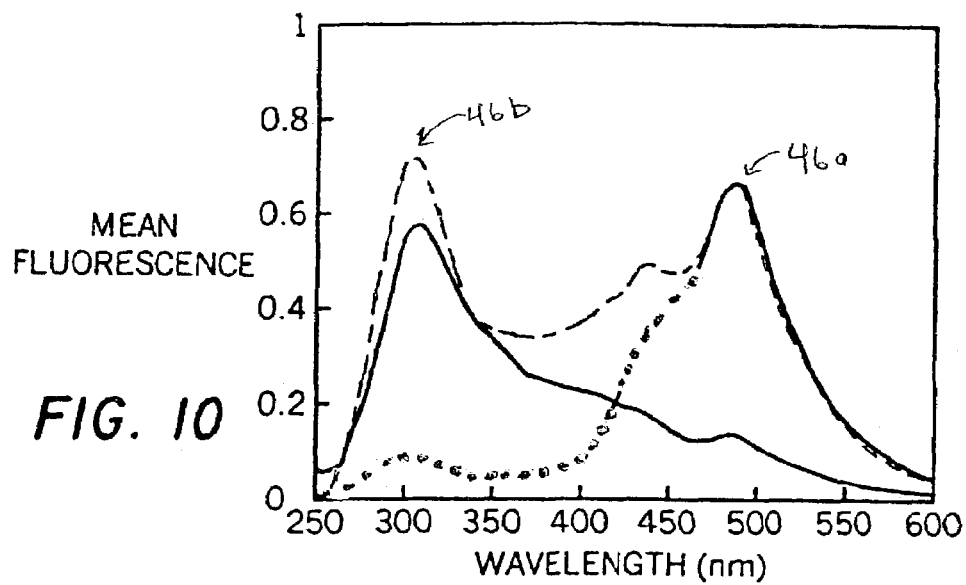
FIG. 10 shows the mean fluorescence spectra of corneas having various concentrations of levofloxacin.

The mean fluorescence spectra are generated for the normal corneas of Example 1, the corneas having a high antibiotic concentration of Example 2, and the corneas having a low antibiotic concentration of Example 3. The normal corneas are represented by the continuous line, those having a high antibiotic concentration are represented by a dashed line, and those having a low antibiotic concentration are represented by a dotted line as shown in FIG. 10.

A comparison of the spectra shows that the addition of levofloxacin to the cornea leads to an increase in the fluorescence at 488 nm. The ratio of mean fluorescence at the first peak 46$a$ of each spectrum (at 488 nm) to the mean fluorescence at the second peak 46$b$ of the same spectrum (at 310 nm) appears to correlate with levofloxacin concentration. The ratio $I_{488}/I_{310}$ ranges from about 0.2 with no levofloxacin present, to 0.9 and 6.7 at its low and high concentrations, respectively.

Figure 11:
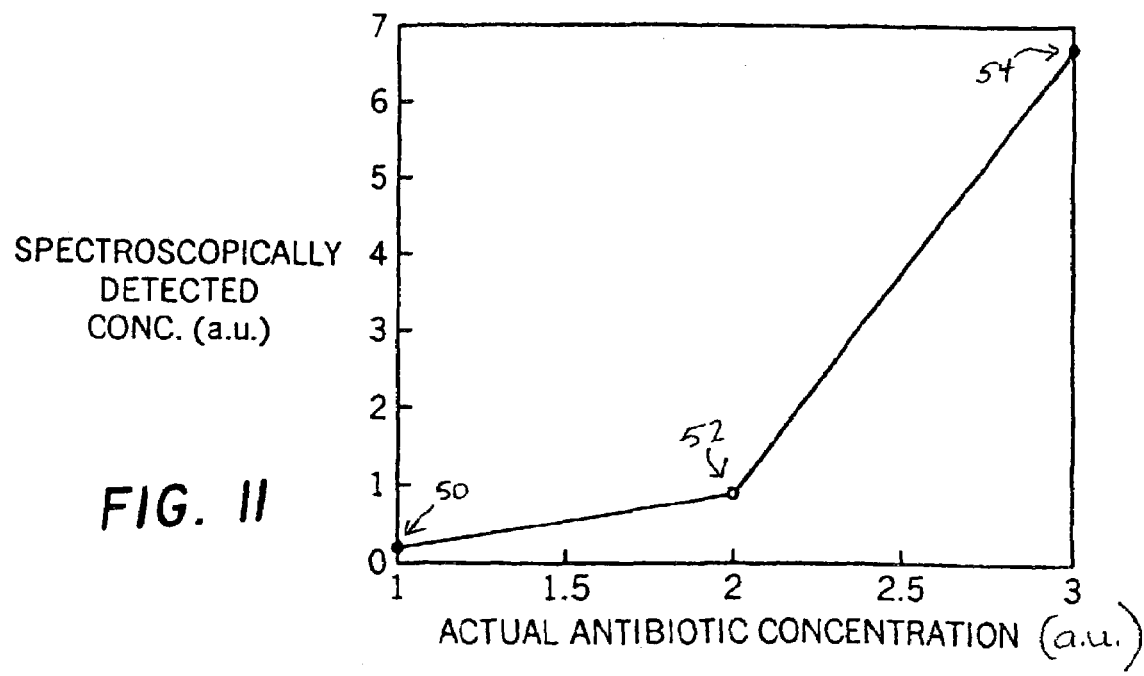
FIG. 11 is a graph showing the concentration of levofloxacin detected in corneal tissue using the spectral analysis system and method of the present invention versus the actual concentration of levofloxacin in the corneal tissue.

FIG. 11 shows the concentration of levofloxacin as detected and calculated using the above ratio versus the actual antibiotic concentration, with the values for the normal cornea, the cornea having a low concentration of antibiotic, and the cornea having a high concentration of antibiotic being indicated at points 50, 52, and 54, respectively. These results show reasonable agreement between the spectroscopically detected concentration and the actual concentration.

Example 8

Laser-induced fluorescence spectroscopy was used to generate fluorescence spectra for balanced saline solution (BSS), an aminoglycoside (tobramycin), and four different fluoroquinolones (ofloxacin, levofloxacin, ciprofloxacin and gatifloxacin). Gatifloxacin is a new $4^{th}$ generation fluoroquinolone.

An aliquot (i.e. 5 drops) of each antibiotic and the BSS was placed in an aluminum container at the focal point of the laser. The solution was then irradiated with the excimer laser and the generated autofluorescence was measured.

Figure 12A:
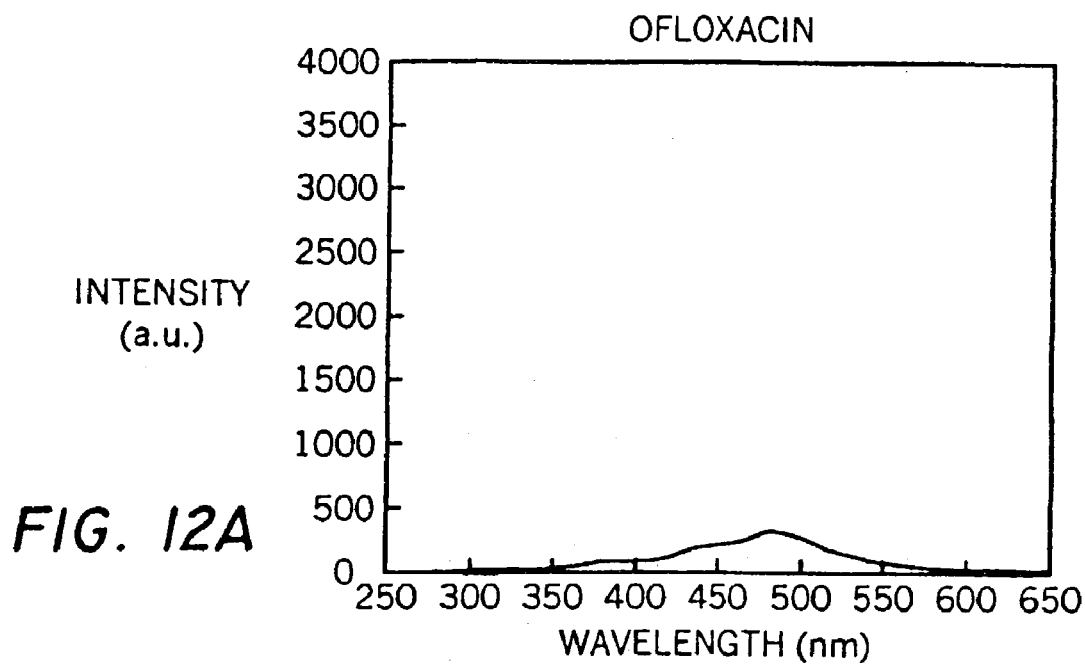
FIGS. 12A-E are graphs showing the fluorescence spectra of ofloxacin, levofloxacin, gatifloxacin, ciprofloxacin, and tobramycin, respectively.
Figure 12B:
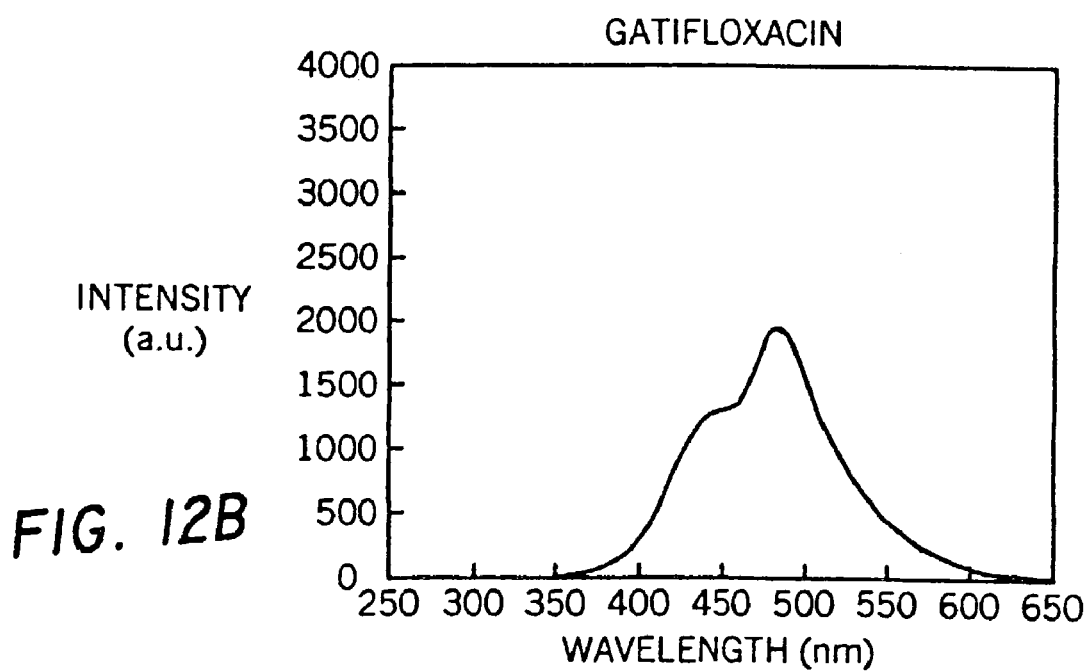
Figure 12C:
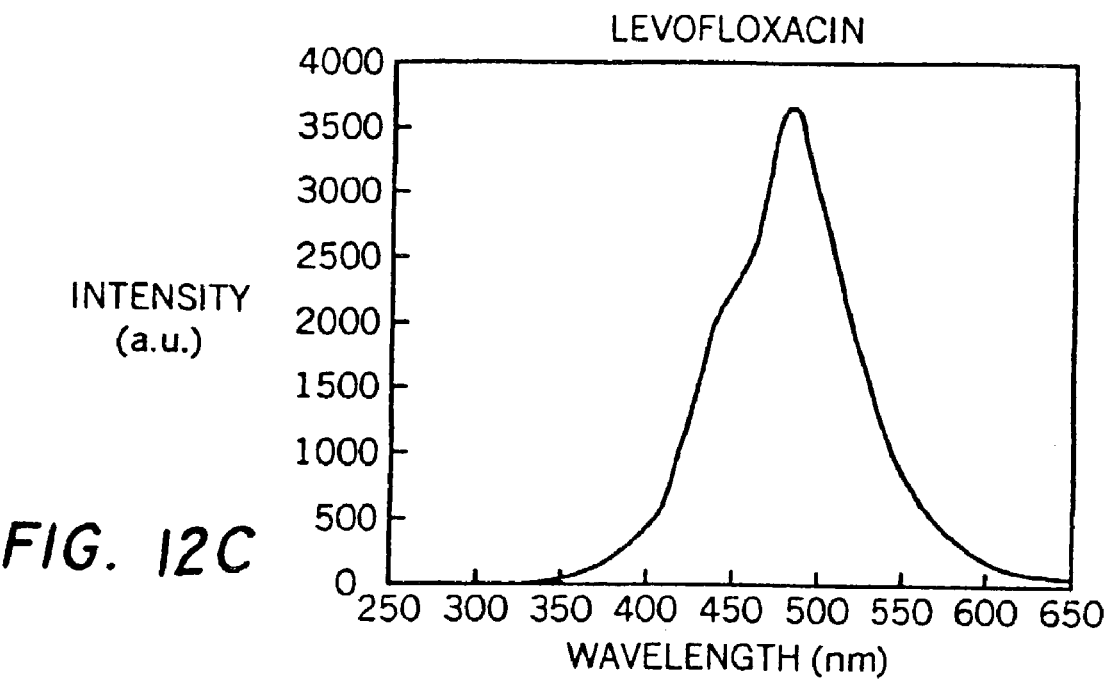
Figure 12D:
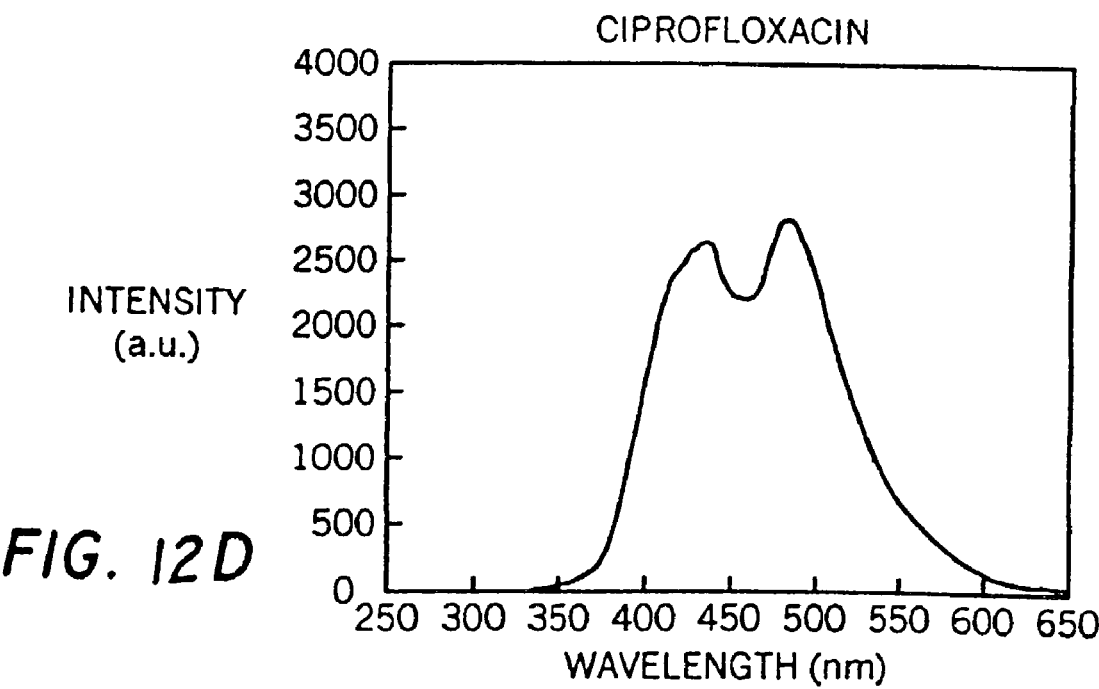

The fluorescence spectra for the fluoroquinolones are shown in FIGS. 12A-D. Each antibiotic exhibited a characteristic fluorescence spectrum with peaks between 400 and 500 nm. Levofloxacin (FIG. 12C) produced the highest fluorescence intensity followed by ciprofloxacin (FIG. 12D), gatifloxacin (FIG. 12B), and ofloxacin (FIG. 12A). The spectral peak of ofloxacin, levofloxacin and gatifloxacin occurred at about 483 nm, while ciprofloxacin exhibited double peaks at about 433 and 483-nm.

Figure 12E:
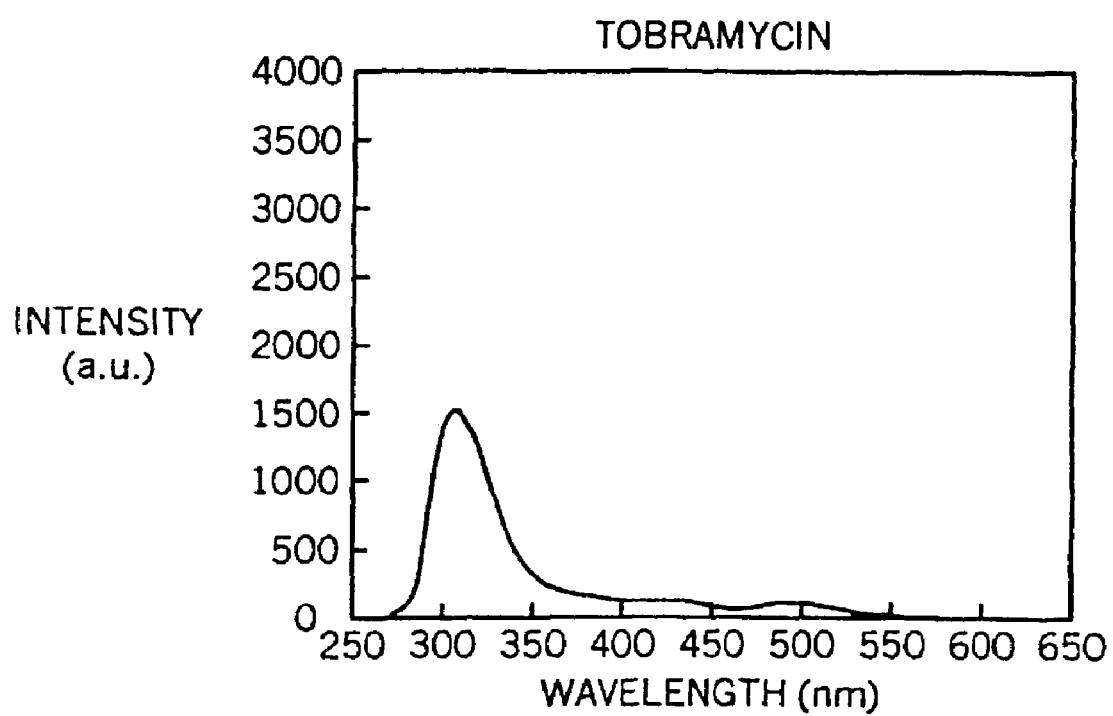

The fluorescence spectrum of tobramycin is shown in FIG. 12E. In contrast to the other four antibiotics, tobramycin exhibited its peak fluorescence at about 300 nm. The fluorescence spectrum of tobramycin coincided with the autofluorescence spectrum of the corneal structural proteins (i.e. elastin and collagen), which prevented its spectroscopic detection in the corneal tissue.

Example 9

The antibiotics listed in Example 8 were administered topically to the globes of 26 rabbits. The applied solution concentrations were as follows: tobramycin (0.3%) (Tobrex, Alcon Laboratories, Fort Worth, Tex.), ofloxacin (0.3%) (Ocuflox, Allergan, Inc., Irvine, Calif.), levofloxacin (0.5%) (Quixin, Santen USA, Inc, Napa, Calif.), ciprofloxacin (0.3%) (Ciloxan, Alcon Laboratories, Inc.) and gatifloxacin (0.3%) (Allergan, Inc., Irvine, Calif.). Sterile balanced salt solution (BSS, Alcon Laboratories, Inc., Fort Worth, Tex.) was used as a negative control.

Four drops of BSS (n=5), tobramycin (n=5), ofloxacin (n=5), levofloxacin (n=3), ciprofloxacin (n=3), or gatifloxacin (n=5) were applied to separate corneas and allowed to sit for 10 minutes. Three drops of the appropriate solution were then administered a second time and globes were allowed to sit for an additional 5 minutes.

In order to wash away excess antibiotic, especially at the corneal surface, each globe was rinsed with approximately 2-ml of lactated Ringer's solution (Baxter Healthcare Corp., Deerfield, Ill.) subsequent to antibiotic administration and prior to laser ablation. After washing, the globes were mounted on the laser platform and the corneas were ablated to perforation.

Figure 13A:
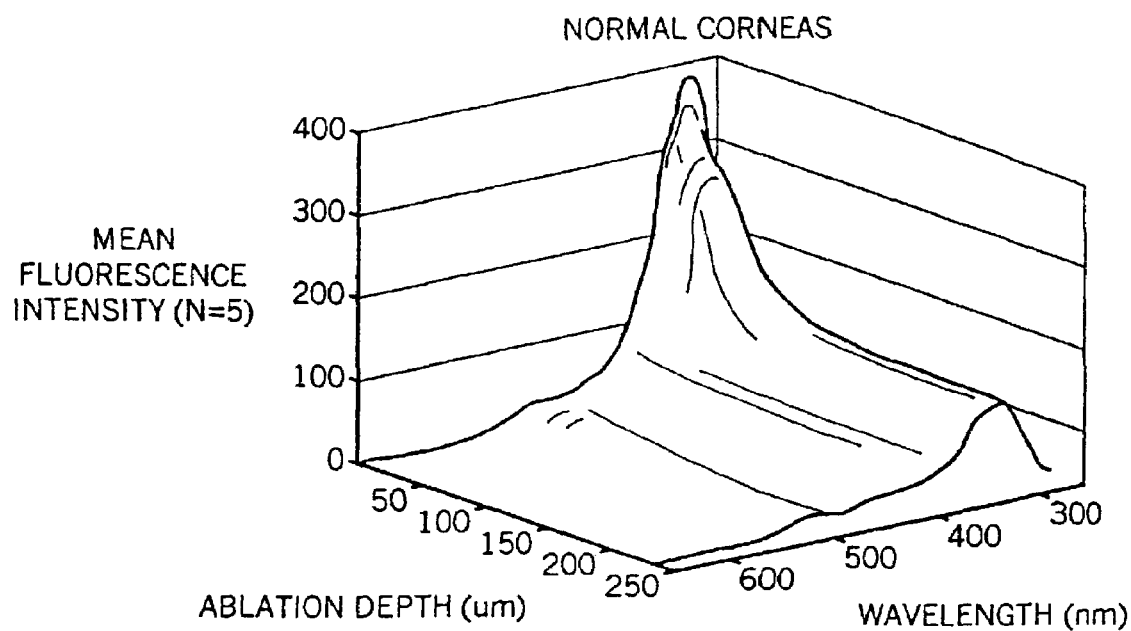
FIGS. 13A and B are graphs showing the mean fluorescence spectra versus ablation depth for (a) normal corneas and (b) tobramycin treated corneas.
Figure 13B:
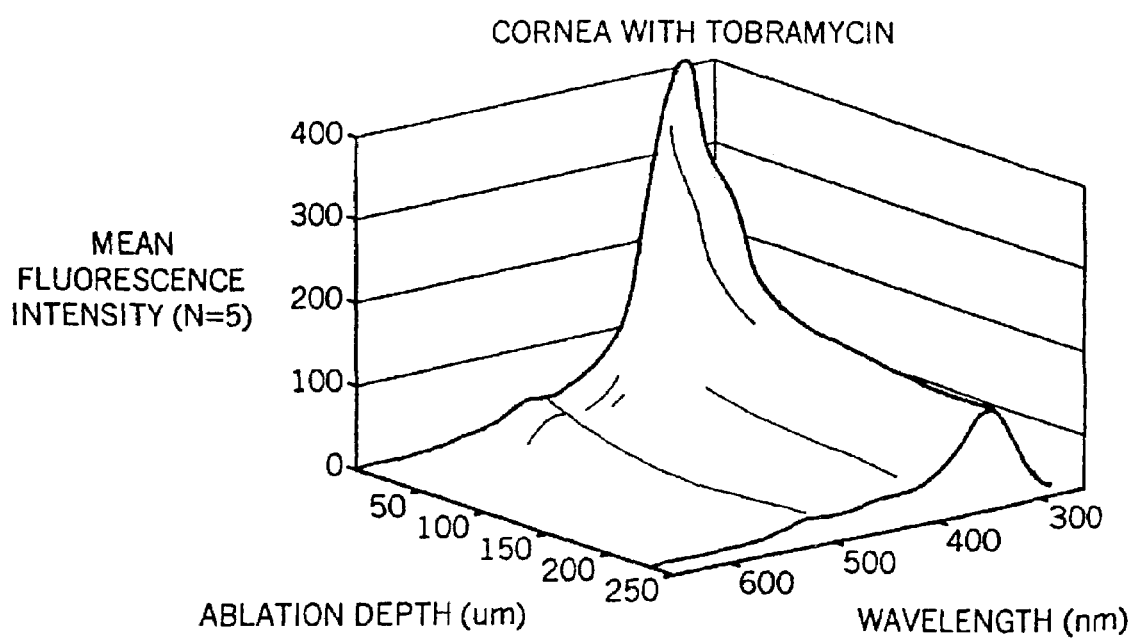
Figure 14A:
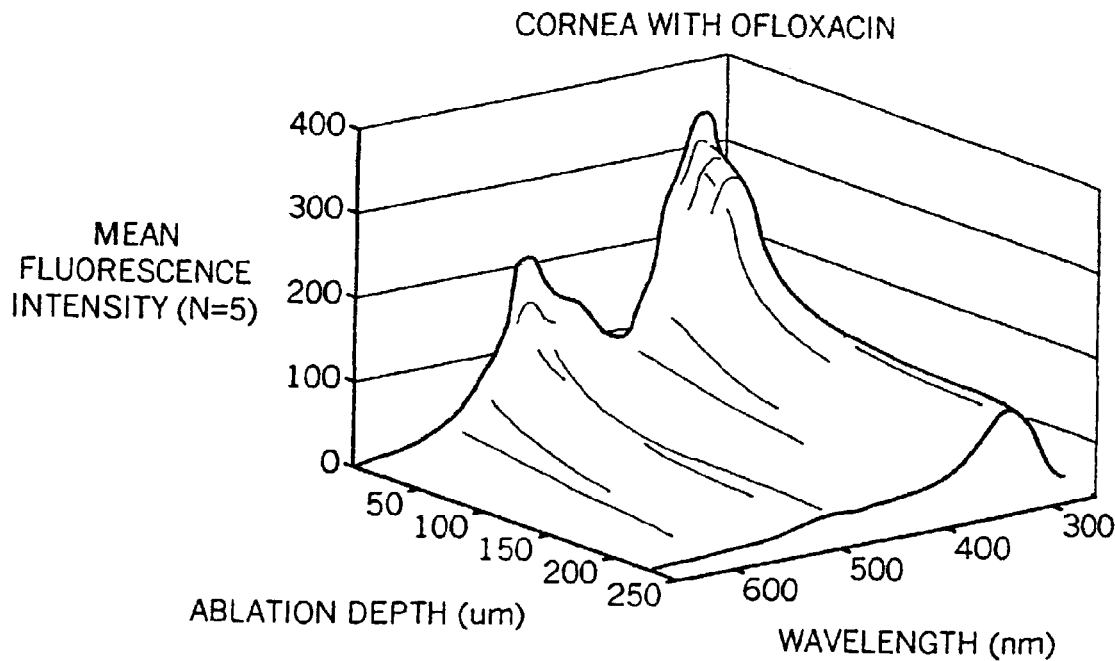
FIGS. 14A and B are graphs showing the mean fluorescence spectra versus ablation depth for (a) ofloxacin treated corneas and (b) levofloxacin treated corneas.
Figure 14B:
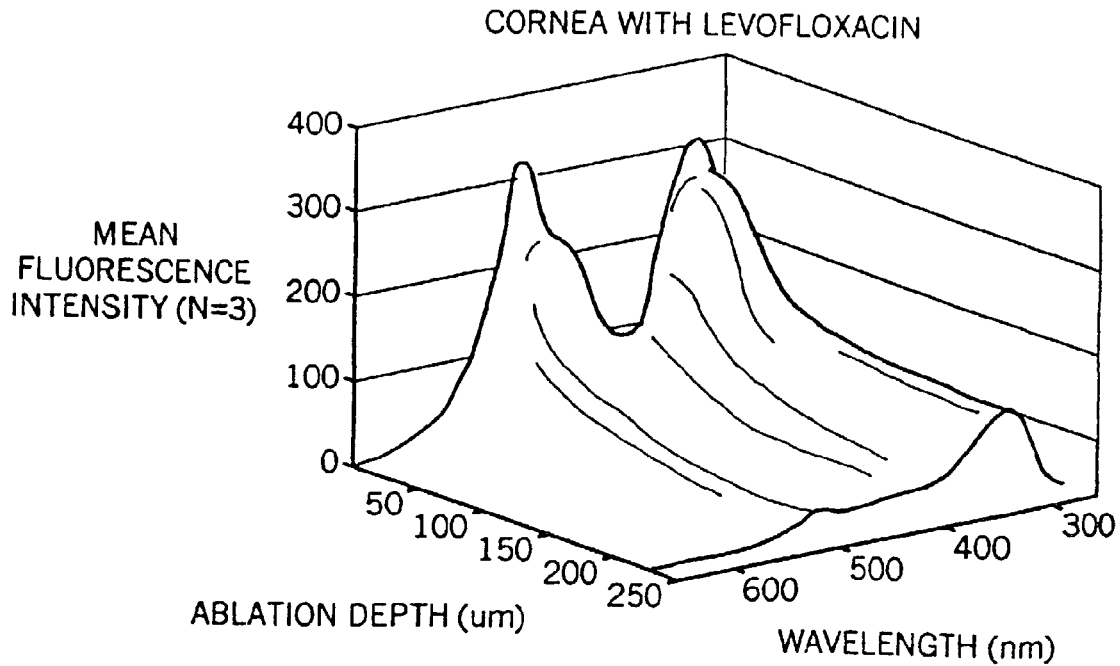
Figure 15A:
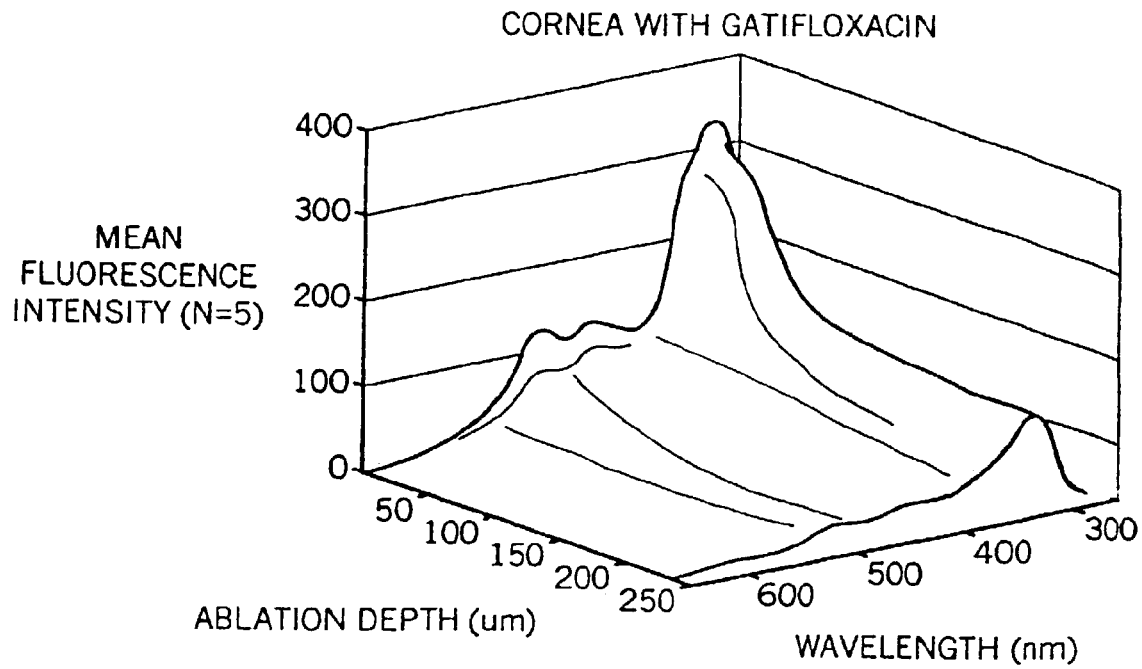
FIGS. 15A and b are graphs showing the mean fluorescence, spectra versus ablation depth for (a) gatifloxacin treated corneas and (b) ciprofloxacin treated corneas.
Figure 15B:
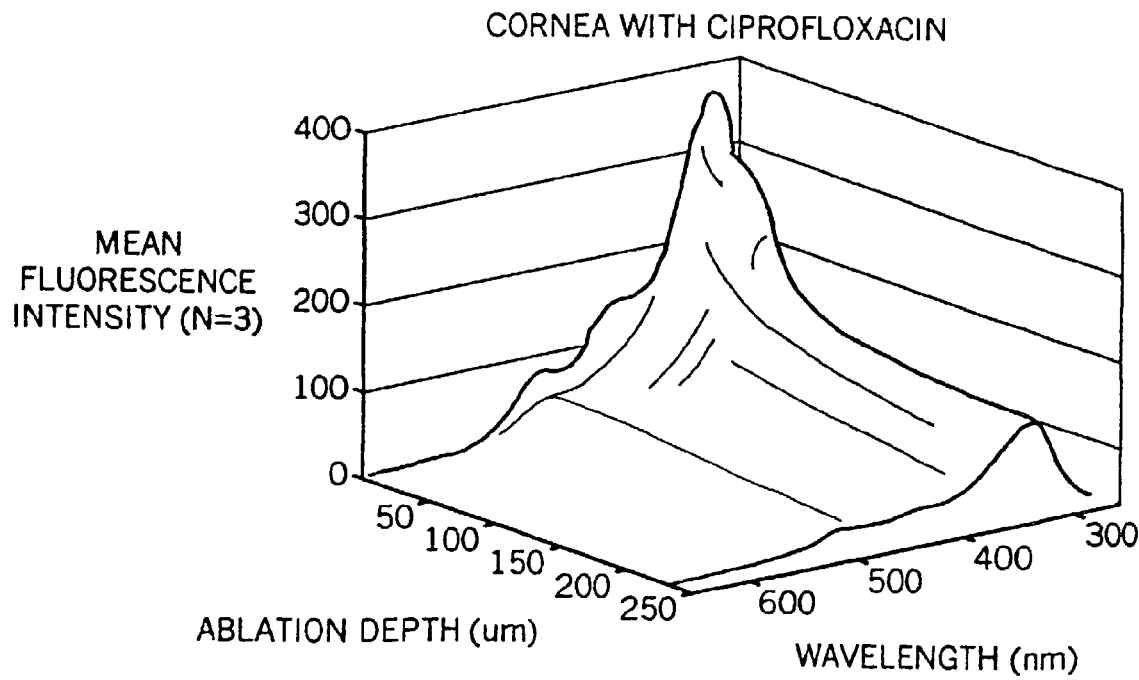

The fluorescence spectra of corneal ablation are plotted versus ablation depth in the three-dimensional plots shown in FIGS. 13A-B, 14A-B, and 15A-B. The corneas treated with tobramycin (FIG. 13B) exhibited a single-peak fluorescence spectrum that is very similar to that of normal cornea (FIG. 13A). On the other hand, the corneas treated with ofloxacin (FIG. 14A), levofloxacin (FIG. 14B), gatifloxacin (FIG. 15A) and ciprofloxacin (FIG. 15B) exhibited a characteristic double-peak fluorescence spectrum. The first peak at about 300-nm coincides with the natural fluorescence of the structural proteins of the corneal tissue while the second peak at about 500-nm coincides with the characteristic fluorescence of the antibiotic.

The maximum penetration depth of the various antibiotics into the corneal tissue is show in Table 1. Ofloxacin penetrated to a detectable depth of 5.9-±2.5 µm, levofloxacin to 5.6-±1.2 µm, ciprofloxacin 1.0±0.5 µm and gatifloxacin 5.8±1.6 µm. The cross-validated detection accuracy of the antibiotic presences was 100% in each case with detection sensitivity of better than 0.06-µg/ml. Under these experimental conditions, none of the fluoroquinolone antibiotics tested appears to have diffused significantly past the intact epithelium. Ofloxacin, levofloxacin and gatifloxacin all appear to penetrate the epithelium significantly more than ciprofloxacin (p<0.02). Tobramycin absorption could not be detected because of the model's inability to discriminate between its fluorescence spectrum and that of the cornea due to their close resemblance.

TABLE 1

Penetration depth of each antibiotic into the corneal tissue.

| Case # | Antibiotic Penetration Depth (μm) | | | |
| --- | --- | --- | --- | --- |
| | Ofloxacin | Gatifloxacin | Levofloxacin | Ciprofloxacin |
| Case 1 | 4.8 | 7.8 | 6.9 | 0.6 |
| Case 2 | 7.2 | N/A | 5.4 | 1.5 |
| Case 3 | 4.2 | 6.3 | 4.5 | 0.9 |
| Case 4 | 9.6 | 4.5 | N/A | N/A |
| Case 5 | 3.6 | 4.5 | N/A | N/A |
| Mean | 5.9 | 5.8 | 5.6 | 1.0 |
| SD | 2.5 | 1.6 | 1.2 | 0.5 |
| Accuracy | 100% | 100% | 100% | 100% |

Other Applications of LIFS System

The successful use of spectroscopy techniques to measure concentrations of antibiotics in corneal tissue has led to the development of a more general spectral analysis system 100 that can be used to measure the absorption of an exogenous material in biological tissue. For instance, the system may be used to accurately measure the absorption of drugs in tissue, cosmetics in skin, and pesticides in produce with sub-micrometer depth resolution.

Figure 16:
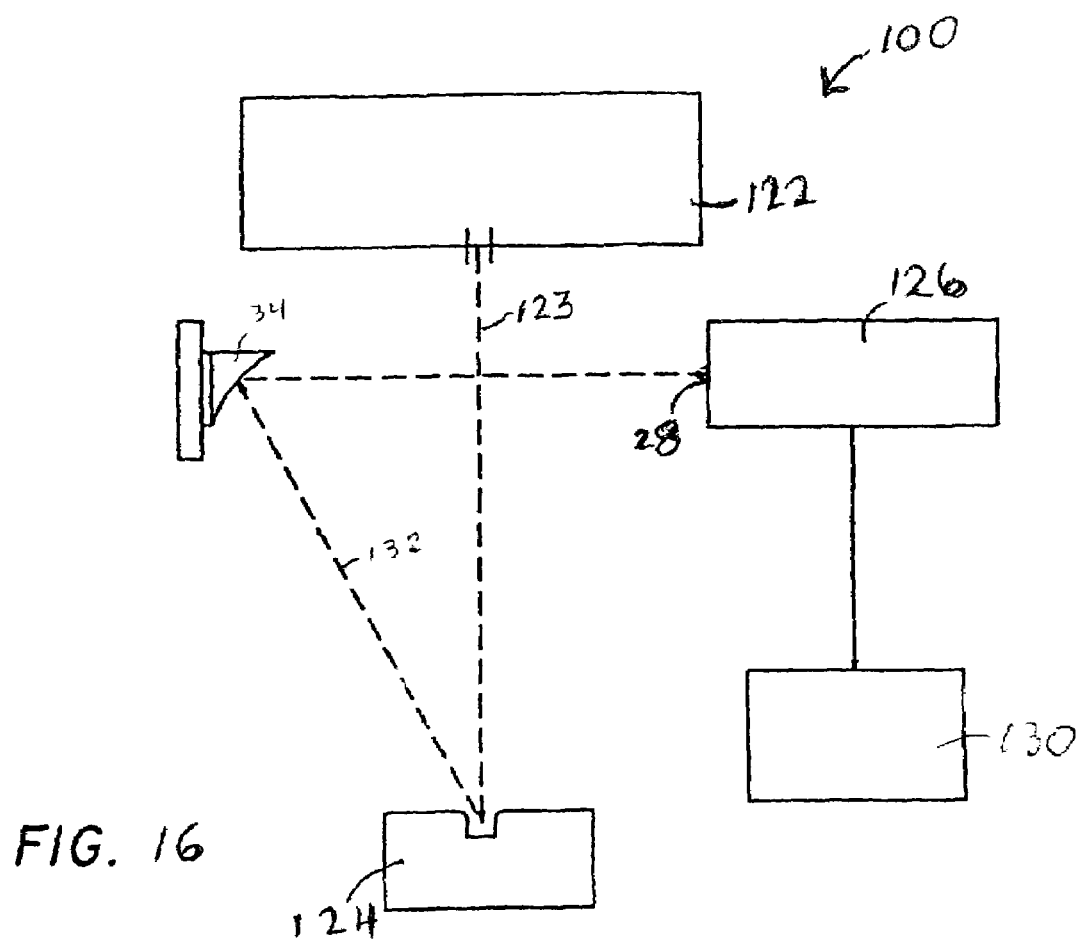
FIG. 16 shows a generalized system for measuring a property of a first material that is present within a second material, according to the principles of the present invention.

The system 100, shown schematically in FIG. 16, comprises fluorescence-inducing means, such as a laser 122, that is operated to emit a collimated laser beam 123 in the direction of a tissue sample 124. The fluorescence 132 produced by the sample 124 is directed, for instance by a mirror 34, into the entrance slit 28 of a spectrograph 126. Data from the spectrograph 126 is then sent to data acquisition means, housed, for instance, in a computer 130. The data may then be processed by any appropriate means, such as an artificial neuron network (ANN).

An ANN is an information-processing paradigm inspired by the densely interconnected, parallel structure of the neurons of the mammalian brain. Essentially, ANNs are made up of collections of mathematical models that emulate some of the observed properties of biological nervous systems and draw on the analogies of adaptive biological learning. A typical ANN paradigm is made up of highly interconnected processing elements that are analogous to neurons. These processing elements are tied together with weighted connections that are analogous to synapses. ANNs are sometimes referred to as connectionist architectures; parallel distributed processing or neuromorphic systems.

Learning or memory in mammalian brains is believed to involve changes in to the synaptic connections that exist between the neurons. Similarly, ANNs are capable of learning through training or exposure to a truthed set of input/output data where the training algorithm iteratively adjusts the connection weights (synapses). These connection weights store the knowledge necessary to solve specific problems.

ANNs are particularly useful as pattern recognition engines and classifiers. Thus, ANNS are useable in computer applications such as voice recognition, signal recognition, as well as functional prediction and system modeling of complex or poorly understood physical processes. ANNs may also be applied to control problems, where the input variables are measurements used to drive an output actuator, and the network learns the control function. The advantage of ANNs lies in their resilience against distortions in the input data and their capability of learning. They are often good at solving problems that are too complex for conventional technologies (e.g., problems that do not have an algorithmic solution or for which an algorithmic solution is too complex to be found) and are often well suited to problems that people are good at solving, but for which traditional methods are not.

FIGS. 4A and B are schematic drawings showing how a spectral analysis system 100 according to the present invention may be integrated into the illumination head 160 of an existing Nidek EC-5000 laser system. The mirror 134 is simply mounted in the distal end of the illumination head 160, to one side of the laser aperture 144, while the spectrograph 126 is mounted on the other side of the laser aperture 144, with its entrance slit 128 facing the mirror 134. The operating microscope 162 at the proximal end of the illumination head 160 may be used by the operator to ensure that the eye 10 or other sample being analyzed is properly aligned with the laser.

Figure 17:
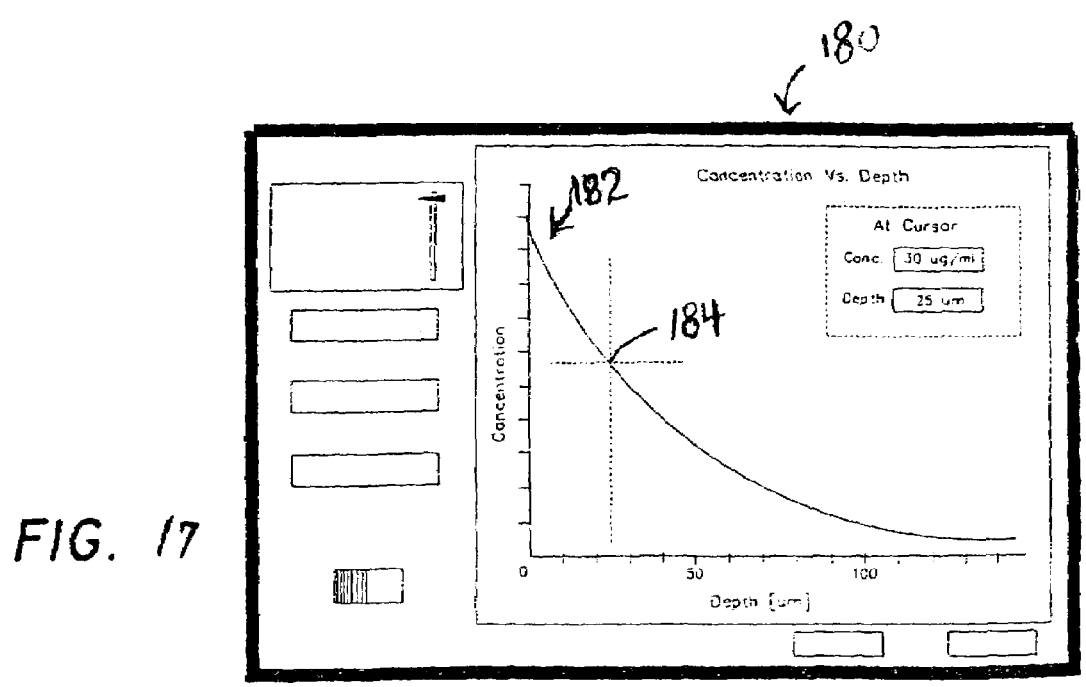
FIG. 17 shows an exemplary display of a spectral analysis system according to the present invention.

A detailed display screen 180 is shown in FIG. 17. This display screen includes a graph 182 showing the concentration of the exogenous material versus its depth in the sample. A moving cursor 184 shows the penetration depth at any given time, and the concentration at that depth. The screen may also display the actual 3-dimensional spectra and other information such as the accuracy of the measurements, the maximum depth of ablation, rate of ablation, crater diameter, and the like.

Although exemplary embodiments of the invention have been shown and described, many changes, modifications and substitutions may be made by those having ordinary skill in the art without necessarily departing from the spirit and scope of this invention. For example, elements, components or attributes of one embodiment or example may be combined with or may replace elements, components or attributes of another embodiment or example to whatever extent is possible without causing the embodiment or example so modified to become unusable for its intended purpose. Accordingly, it is intended that all such additions, deletions, modifications and variations be included within the scope of the following claims. Also, although several illustrative examples of means for practicing the invention are described above, these examples are by no means exhaustive of all possible means for practicing the invention. The scope of the invention should therefore be determined with reference to the appended claims, along with the full range of equivalents to which those clams are entitled.

The invention claimed is:

1. A system for determining the presence and/or concentration of an exogenous substance in a material, said system comprising:
    a) an energy-emitting device which projects a flow of energy onto or into the material, said energy being effective to i) ablate at least some of the material and ii) cause the exogenous substance, if present within the ablated material, to emit fluorescence;
    b) a spectrum generating device which generates fluorescence spectra on the basis of the fluorescence emitted by the exogenous substance; and
    c) a spectral processing device, which uses the fluorescence spectra to determine the presence or concentration of the substance, said spectral processing device comprising; i) means for collecting and saving data from the spectrograph, ii) means for identifying first and second spectral peaks corresponding to first and second wavelengths on the spectrum, iii) means for calculating a ratio between the fluorescence at the second spectral peak and the fluorescence at the first spectral peak and for determining the concentration based on the ratio and iv) output means for displaying the concentration.

2. A system according to claim 1, wherein the energy-emitting device comprises a device for directing laser energy onto or into the material.

3. A system according to claim 1, wherein the spectrum generating device comprises a fluorescence spectrograph.

4. A system according to claim 1, wherein the spectral processing device comprises a microprocessor.

5. A system according to claim 4, wherein the material is selected from the group consisting of: biological tissue, plant matter, a vegetable, a fruit, an admixture and a mass of solid matter.

6. A method for determining the presence or concentration of an exogenous substance in a material, comprising the steps of:
   a) directing ablative energy onto or into the material to i) ablate at least a portion of the material and ii) cause the exogenous substance to fluoresce;
   b) directing the fluorescence into a spectrograph to generate at least one fluorescence spectrum;
   c) processing the fluorescence spectrum obtained in Step B to determine the presence or concentration of the exogenous substance in the ablated material by i) measuring the fluorescence at a first peak within a spectrum, ii) measuring the fluorescence at a second peak within the same spectrum and iii) calculating a ratio between the fluorescence at the first peak and the fluorescence at the second peak, the ratio being indicative of the concentration of the exogenous substance in the material.

7. A method according to claim 6 wherein the material comprises at least first and second layers and wherein:
   Step A comprises directing the ablative energy so as to ablate at least a portion of the first layer and at least a portion of at least one additional layer to cause fluorescence of any of the endogenous substance contained in the ablated portions of said first and said at least one additional layer;
   Step B comprises generating a first fluorescence spectrum from fluorescence received from the first layer and additional fluorescence spectra from fluorescence received from each additional layer; and
   Step C comprises calculating the correlation-coefficient between the first fluorescence spectrum and at least one additional fluorescence spectrum, the correlation-coefficient being indicative of difference in concentration of the exogenous substance between the ablated portion of the first layer and the ablated portion of at least one additional layer.

8. A method according to claim 7 wherein Step C comprises determining decorrelation between the first fluorescence spectrum and at least one additional fluorescence spectrum to determine the difference in concentration of the exogenous substance between the ablated portion of the first layer and the ablated portion of at least one additional layer.

9. A method according to claim 6 wherein the material comprises at least first and second layers and wherein:
   Step A comprises directing the ablative energy so as to ablate at least a portion of the first layer and at least a portion of at least one additional layer causing fluorescence of any of the endogenous substance contained in the ablated portions of said first and said at least one additional layer;
   Step B comprises generating a first fluorescence spectrum from fluorescence received from the first layer and additional fluorescence spectra from fluorescence received from each additional layer; and
   Step C comprises calculating the sum of absolute differences (SAD) between the first fluorescence spectrum and at least one subsequent fluorescence spectrum, the SAD being indicative of the difference in concentration of the exogenous substance between the ablated portion of the first layer and the ablated portion of at least one additional layer.

10. A method according to claim 6 wherein the material comprises at least first and second layers and wherein:
    Step A comprises directing the ablative energy so as to ablate at least a portion of the first layer and at least a portion of at least one additional layer to cause fluorescence of any of the endogenous substance contained in the ablated portions of said first and said at least one additional layer;
    Step B comprises generating a first fluorescence spectrum from fluorescence received from the first layer and additional fluorescence spectra from fluorescence received from each additional layer; and
    Step C comprises comparing the kurtosis of the first fluorescence spectrum to the kurtosis of at least one additional fluorescence spectrum to determine the difference in concentration of the exogenous substance between the ablated portion of the first layer and the ablated portion of at least one additional layer.

11. A method according to claim 6 wherein the material comprises a first layer and at least one additional layer and wherein:
    Step A comprises directing the ablative energy so as to ablate at least a portion of the first layer and at least a portion of at least one additional layer to cause fluorescence of any of the endogenous substance contained in the ablated portions of said first and said at least one additional layer;
    Step B comprises generating a first fluorescence spectrum from fluorescence received from the first layer and additional fluorescence spectra from fluorescence received from each additional layer; and
    Step C comprises comparing the skewness of the first fluorescence spectrum to the skewness of at least one additional fluorescence spectrum to determine the difference in concentration of the exogenous substance between the ablated portion of the first layer and the ablated portion of at least one additional layer.

12. A method according to claim 6 wherein the material comprises a first layer and at least one additional layer and wherein:
    Step A comprises directing the ablative energy so as to ablate at least a portion of the first layer and at least a portion of at least one additional layer to cause fluorescence of any of the endogenous substance contained in the ablated portions of said first and said at least one additional layer;
    Step B comprises generating a first fluorescence spectrum from fluorescence received from the first layer and additional fluorescence spectra from fluorescence received from each additional layer; and
    Step C comprises comparing the percentile of the first fluorescence spectrum to the percentile of at least one additional fluorescence spectrum to determine the difference in concentration of the exogenous substance between the ablated portion of the first layer and the ablated portion of at least one additional layer.

13. A method according to claim 6, wherein the material comprises body tissue from a living or cadaveric body.

14. A method according to according 13, wherein the tissue is corneal tissue.

15. A method according to claim 6, wherein the exogenous substance is a drug.

16. A method according to claim 6, wherein the exogenous substance comprises an antibiotic.

17. A method according to claim 16, wherein the antibiotic comprises a fluoroquinolone.

18. A method for determining the presence or concentration of an exogenous substance in a material, comprising the steps of:
   a) directing ablative energy onto or into the material to i) ablate at least a portion of the material and ii) cause the exogenous substance to fluoresce;
   b) directing the fluorescence into a spectrograph to generate at least one fluorescence spectrum;
   c) processing the fluorescence spectrum obtained in Step B to determine the presence or concentration of the exogenous substance in the ablated material;
      wherein the material comprises corneal tissue and wherein the method determines the presence or concentration of a fluoroquinolone antibiotic in at least one layer of the corneal tissue.

19. A method according to claim 6 or 18, wherein the energy delivered in Step A is laser energy.

20. A method according to claim 19 wherein the laser energy is in the ultraviolet band.

21. A method according to claim 19 wherein the laser energy is pulsed.

22. A method according to claim 6 or 18, wherein the Step A comprises directing ablative laser energy from an excimer laser onto or into the material.

23. A method of detecting concentrations of an exogenous substance in a material as a function of depth in the material, said method comprising the steps of:
   a) ablating a quantity of the material to a desired depth;
   b) causing the substance to emit fluorescence as the material is being ablated;
   c) determining the presence or concentration of the substance in the material at a plurality of different depths through which the ablation has extended;
   d) plotting the concentration of the substance versus the ablation to determine an absorption gradient;
      wherein the substance and material are selected from the group consisting of: i) the substance being a pesticide or herbicide and the material being a food product or ii) the substance being a cosmetic and the material being skin.

24. A method according to claim 23, wherein the steps of ablating the material and inducing fluorescence in the material are performed concurrently by directing laser energy at the material.

25. A method according to claim 23, wherein the step of detecting the concentration of the fluorescent substance comprises:
   a) directing the fluorescence emitted from the sample into a spectrograph to generate a fluorescence spectrum; and
   b) processing the spectrum using techniques selected from the group consisting of spectral classification techniques, partial least squares modeling and neural networking.

* * * * *